United States Patent [19]

Marfat

[11] Patent Number: 4,914,101
[45] Date of Patent: Apr. 3, 1990

[54] 3,4-DIHYDRO-2-ALKYL-3-OXO-N-ARYL-2H-(1)BENZO-THIENO(3,2-E)-1,2-THIAZINE-4-CARBOXAMIDE-1,1-DIOXIDES

[75] Inventor: Anthony Marfat, Mystic, Conn.

[73] Assignee: Pfizer Inc., New York, N.Y.

[21] Appl. No.: 382,161

[22] PCT Filed: Jun. 10, 1987

[86] PCT No.: PCT/US87/01357
§ 371 Date: Feb. 6, 1989
§ 102(e) Date: Feb. 6, 1989

[87] PCT Pub. No.: WO88/09793
PCT Pub. Date: Dec. 15, 1988

[51] Int. Cl.4 .................. C07D 513/04; C07D 495/04; A61K 31/54
[52] U.S. Cl. ..................... 514/229.8; 544/33
[58] Field of Search .................. 544/33; 514/229.8

[56] References Cited

U.S. PATENT DOCUMENTS

| | | | |
|---|---|---|---|
| 3,591,584 | 7/1971 | Lombardino | 544/48 |
| 4,076,709 | 2/1978 | Hromatka et al. | 544/48 |
| 4,187,303 | 2/1980 | Hromatka et al. | 544/48 |
| 4,259,336 | 3/1981 | Engel et al. | 544/33 |

FOREIGN PATENT DOCUMENTS 0021058 1/1981 European Pat. Off. .
2002771 2/1979 United Kingdom .

OTHER PUBLICATIONS

Numanov, Chemical Abstracts; vol. 80(1), No. 3333Y (Jan. 1974).
Nasyrov, Chemical Abstracts, vol. 81(17), No. 105154D (Oct. 1974).
Jakschick, Prostaglandins (16), 733-747 (1978).
Jakschick, Biochem. Biophys. Res. Commun. (95), 103-110 (1980).
Lombardino et al., J. Med. Chem. Vol. 14, No. 12, pp. 1171-1175 (1971).
Winter et al., Proc. Soc. Exp. Biol. Med., vol. 111, pp. 544-547 (1962).
Radzhabov et al., Chemical Abstracts, vol. 84, No. 89931j (1976).
Siegmund et al., Proc. Soc. Exp. Biol. Med., vol. 95, pp. 727-731 (1957).
Lombardino et al., J. Med. Chem., vol. 14, No. 10, pp. 973-977 (1971).

Primary Examiner—John M. Ford
Attorney, Agent, or Firm—Peter C. Richardson; Paul H. Ginsburg; Karen DeBenedictis

[57] ABSTRACT

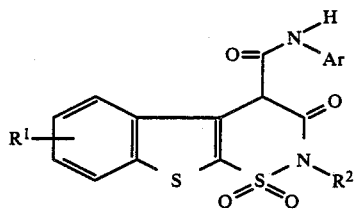

and pharmaceutically acceptable salts thereof,
wherein
$R^1$ is hydrogen, halogen or $C_1$ to $C_4$ alkyl;
$R^2$ is hydrogen or $C_1$ to $C_4$ alkyl; and Ar is phenyl or phenyl substituted with one or more substituents selected from $C_1$ to $C_4$ alkyl, halo, trifluoromethyl, nitro, hydroxyl, halophenyl, or $C_1$ to $C_4$ alkoxy.

The compounds are useful in treating inflammation or other prostaglandin or leukotriene mediated diseases.

14 Claims, No Drawings

3,4-DIHYDRO-2-ALKYL-3-OXO-N-ARYL-2H-(1)BENZO-THIENO(3,2-E)-1,2-THIAZINE-4-CARBOXAMIDE-1,1-DIOXIDES

BACKGROUND OF THE INVENTION

The present invention relates to 3,4-dihydro-2-alkyl-3-oxo-N-aryl-2H-[1]benzothieno[3,2-e]-1,2-thiazine-4-carboxamide-1,1-dioxides, methods of preparing such compounds, pharmaceutical compositions comprising such compounds and the use of such compounds in treating inflammation (e.g., arthritis) or other prostaglandin or leukotriene mediated diseases.

SUMMARY OF THE INVENTION

The present invention relates to compounds of the formula

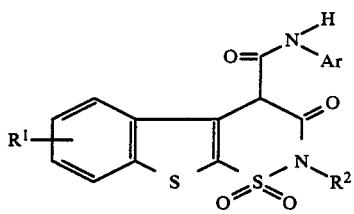

and pharmaceutically acceptable salts thereof wherein $R^1$ is hydrogen, halogen or $C_1$ to $C_4$ alkyl;

$R^2$ is hydrogen or $C_1$ to $C_4$ alkyl; and Ar is phenyl or phenyl substituted with one or more substituents selected from $C_1$ to $C_4$ alkyl, halo, trifluoromethyl, nitro, hydroxyl, halophenyl, or $C_1$ to $C_4$ alkoxy.

The present invention also relates to a pharmaceutical composition useful in the treatment of inflammation or other prostaglandin or leukotriene mediated diseases comprising an amount of a compound of the formula I effective to treat inflammation or another prostaglandin or leukotriene mediated disease and a pharmaceutically acceptable carrier.

The present invention also relates to a method of treating a prostaglandin or leukotriene mediated disease comprising administering to a patient in need of such treatment a compound of formula I in an amount effective to treat such disease.

The present invention also relates to intermediates useful in preparing the foregoing compounds and to methods of preparing the foregoing compounds.

A preferred embodiment of the invention relates to compounds of the formula I wherein $R^1$ is hydrogen. Another preferred embodiment relates to compounds of the formula I wherein $R^2$ is methyl. In a more preferred embodiment, $R^1$ is hydrogen and $R^2$ is methyl.

Specific preferred compounds of the present invention include the following:

3,4-Dihydro-2-methyl-1,3-oxo-N-phenyl-2H-[1]benzothieno[3,2-e]-1,2-thiazine-4-carboxamide-1,1-dioxide;

N-(4-Fluorophenyl)-3,4-dihydro-2-methyl-1,3-oxo-2H-[1]benzothieno[3,2-e]-1,2-thiazine-4-carboxamide-1,1-dioxide;

N-(4-Bromophenyl)-3,4-dihydro-2-methyl-1,3-oxo-2H-[1]benzothieno[3,2-e]-1,2-thiazine-4-carboxamide-1,1-dioxide;

N-(4-trifluoromethylphenyl)-3,4-dihydro-2-methyl-1,3-oxo-2H-[1]benzothieno[3,2-e]-1,2-thiazine-4-carboxamide-1,1-dioxide;

N-(2-Methyl-4-nitrophenyl)-3,4-dihydro-2-methyl-1,3-oxo-2H-[1]benzothieno[3,2-e]-1,2-thiazine-4-carboxamide-1,1-dioxide; and N-(2,4Difluorophenyl)-3,4-dihydro-2-methyl-1,3-oxo-2H[1]benzothieno[3,2-e]-1,2-thiazine-4-carboxamide-1,1-dioxide.

Other compounds of the present invention are compounds of the formula I wherein $R^1$ is H, $CH_3$, Cl, F, $CF_3$, $NO_2$, Br, methoxy, or H; $R^2$ is H, $CH_3$, $C_2H_5$, or benzyl; and Ar is substituted phenyl such as 2,4-dichlorophenyl, 4-chlorophenyl, methoxyphenyl, nitrophenyl or trifluoromethylphenyl.

DETAILED DESCRIPTION OF THE INVENTION

The compounds of formula I may be prepared as shown below in Scheme 1. The compounds of formulae IV, V and VI disclosed in the scheme are novel compounds.

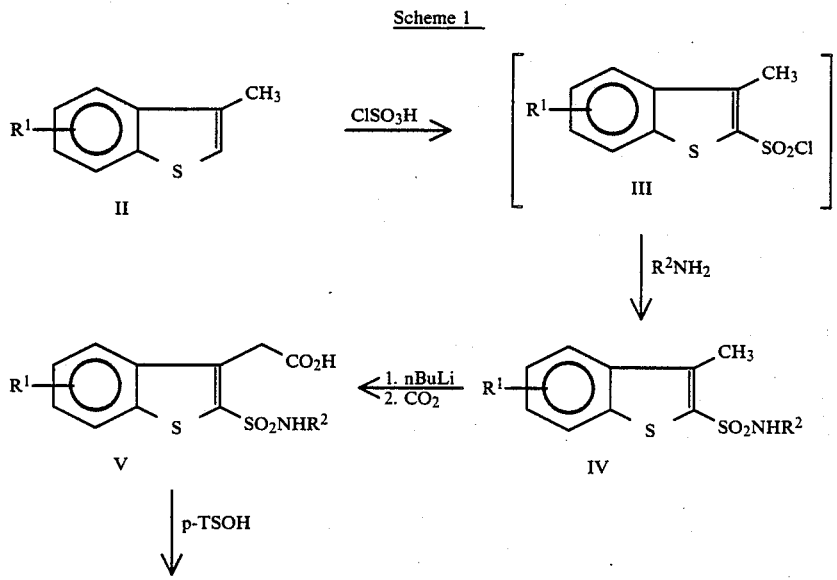

Scheme 1

Scheme 1

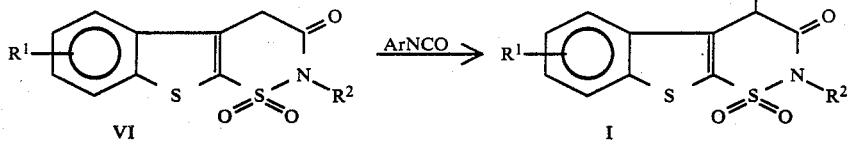

Thus, chlorosulfonation of 3-methylbenzo[b]thiophene (II) followed by reaction of the intermediate sulfonyl chloride (III) with a $C_1$–$C_6$ alkylamine (preferably, methylamine) provides IV. The solvent for both reactions should be a chlorinated solvent, for example, methylene chloride or dichloroethane. The preferred solvent is methylene chloride. The temperature of the reaction medium for the chlorosulfonation reaction should be about −20° to about 50° C., preferably about 0° C. The temperature of the reaction medium for the second reaction should be about −10° to about 50° C., preferably about 0° C. The pressure of the reaction medium for the foregoing two reactions is not critical. For example, it may be about 0.1 to about 10 atmospheres. The pressure is preferably ambient pressure, i.e. about one atmosphere.

Lithiation of IV followed by quenching the resultant dianion with gaseous carbon dioxide provides, after acidification, V. An aryllithium (e.g., phenyllithium) or alkyllithium (e.g., methyllithium, ethyllithium, sec-butyllithium, or t-butyllithium) is used to effect lithiation. The preferred reagent is n-butyllithium. The solvent for the lithiation reaction should be an aprotic solvent, for example, tetrahydrofurane, dioxane or dimethoxyethane. The preferred solvent is ethyl ether. The temperature of the reaction medium for the lithiation reaction should be about −50° to about 50° C., preferably about −20° to about 0° C. The pressure is not critical. For example, it may be about 0.1 to about 10 atmospheres. The pressure is preferably ambient pressure, i.e. about one atmosphere.

Cyclodehydration of V in the presence of an acid provides VI. The preferred acid is p-toluenesulfonic acid. The solvent for the cyclodehydration reaction should be a neutral solvent having a high boiling point, for example, benzene or toluene. The preferred solvent is xylene. The temperature of the reaction medium for the cyclodehydration reaction should be about 25 to about 250° C., preferably the reflux temperature of the chosen solvent. The pressure is not critical. For example, it may be about 0.1 to about 10 atmospheres. The pressure is preferably ambient pressure, i.e., about one atmosphere.

Reaction of VI with an aryl isocyanate in a polar solvent (e.g. dimethylsulfoxide) gives a compound of formula I. The aryl isocyanate is a compound of the formula ArNCO wherein Ar is as defined above. The preferred solvent is dimethylformamide. The temperature of the reaction medium for the foregoing reaction should be about −20° to about 100° C., preferably ambient temperature, i.e. about 20° C. The pressure is not critical. For example, it may be about 0.1 to about 10 atmospheres. The pressure is preferably ambient pressure, i.e. about one atmosphere.

Salts of compounds of the formula I may be prepared in a conventional manner by reacting a compound of the formula I with an appropriate acid or base, for example, an inorganic base such as an alkali metal hydroxide or an alkaline earth metal hydroxide or an acid such as phosphoric acid or hydrochloric acid.

The activity of the compounds of formula I in the treatment of pulmonary, asthmatic, allergic and inflammatory diseases may be determined by a standard test measuring an agent's ability to inhibit cyclooxygenase and 5-lypoxygenase enzyme activity of rat basophil leukemia (RBL-1) cells. According to this test as described by Jakschick et al., *Prostaglandins,* 16, 733–747 (1978), and Jakschick et al., *Biochem. Biophys. Res. Commun.,* 95, 103–110 (1980), a monolayer of RBL-1 cells is grown for 1 or 2 days in spinner culture in Eagle's minimum essential medium, 15% heat-inactivated fetal calf serum and an antibiotic/antimycotic mixture. The cells are washed after centrifugation and incubated in a buffer. A volume of 0.5 ml of cell suspension is preincubated at 30° C. for ten minutes with a 1 microliter dimethylsulfoxide (DMSO) solution of the agent to be tested. The incubation is initiated by simultaneous addition of 5 microliters ($^{14}$C)-arachidonic acid in ethanol and 2 microliters calcium ionophore (A-21387) in DMSO for final concentrations of 5 and 7.6 micromolar, respectively. Five minutes later, the incubation is terminated by the addition of 0.27 ml acetonitrile/acetic acid (100:3). High pressure liquid chromatography is performed using acetonitrile/water/acetic acid solvent. Radiolabeled prostaglandin $D_2$ ($PGD_2$), leukotrine $B_4$ ($LTB_4$), 5-hydroxyeicosatetraenoic acid (5-HETE), and unreacted arachidonic acid are determined. The inhibitory effect on the cyclooxygenase pathway is assessed from the reduction of $PGD_2$ levels and the inhibitory effect on the 5-lipoxygenase pathway is assessed from the decrease in the amount of $LTB_4$ and 5-HETE.

The compounds of the formula I and their pharmaceutically acceptable salts are effective inhibitors of mammalian leukotriene or prostaglandin biosynthesis or both and are thus useful in the treatment of various leukotriene or prostaglandin mediated conditions. In particular, the compounds have utility, both as the sole active agent and also in combination with other active agents, for the treatment of various pulmonary, gastrointestinal, inflammatory, dermatological and cardiovascular conditions such as inflammation, arthritis, allergy, psoriasis, asthma, bronchitis, pulmonary hypertension and hypoxia, peptic ulcers, inflammatory bowel disease or cardiovascular spasm, such as acute myocardial infarctions, and the like in mammals, especially in humans. The compounds of the formula I and their pharmaceutically acceptable salts are particularly useful in treating arthritis.

For treatment of the various conditions described above, the compounds of formula I and their pharmaceutically acceptable salts may be administered to a subject in need of treatment by a variety of conventional routes of administration, including oral, by injection, topical, rectal, and in an aerosol carrier composition for administration by inhalation.

The exact dosage of a compound of the present invention will depend upon such factors as the age, weight and condition of the patent and the severity of disease. In general, however, a therapeutically-effective dose of a compound of formula I or a pharmaceutically acceptable salt thereof will range from 0.01 to 100 mg/kg body weight of the subject to be treated per day, preferably 0.1 to 50 mg/kg per day.

Although the compounds of formula I and their pharmaceutically acceptable salts can be administered alone, they will generally be administered in admixture with a pharmaceutical carrier selected with regard to the intended route of administration and standard pharmaceutical practice. For example, oral administration may be in the form of tablets containing such excipients as starch or lactose, or in the form of elixirs or suspensions containing flavoring or coloring agents. In the case of animals, the compounds of the present invention are advantageously contained in an animal feed or drinking water. For parenteral injection, they amy be used in the form of a sterile aqueous solution which may contain other solutes, for example, enough salt or glucose to make the solution isotonic. Other active compounds, including NSAIDS (non-steroidal antiinflammatory drugs) may be administered along with the compounds of the present invention.

The following non-limiting Examples are illustrative of the compounds of the present invention. All melting points referred to in the Examples are uncorrected.

EXAMPLE 1

N-3-Dimethyl-benzo[b]thiophene-2-sulfonamide

To a solution of 3-methylbenzo[b]thiophene (20.0 g, 125.1 mmoles) in chloroform (300 ml, was added dropwise chlorosulfonic acid (22.4 ml), 39.6g, 337.9 mmoles) at −5° C. The reaction mixture was stirred at 0° C. for 3 hours, and dry methylamine gas was then bubbled in at 0° C. for 3 hours. The reaction mixture was slowly warmed to ambient temperature and then stirred overnight. The mixture was diluted with ethyl acetate, then washed with dilute hydrochloric acid and water, dried (magnesium sulfate), and concentrated in vacuo to give an oil. This oil was chromatographed on silica gel, eluting with ethyl acetate:methylene chloride (1:39 by volume) to give 5.0 g (15%) of the title compound. Trituration using ether:hexane gave an analytically pure compound, mp 124°–127° C.; ms:m/e 241 (m+,21), 176(13), 162(24), 146(100); $^1$H-nmr(deuteriochloroform):δ7.85 (m,2H), 7.50 (m,2H), 4.64 (m,1H), 2,80 (d,3H), 2.72 (s,3H); ir(potassium bromide):3298 cm$^{-1}$.

Anal. Calcd. for $C_{10}H_{11}NO_2S_2$: C, 49.77; H, 4.59; N, 5.80. Found: C, 49.66; H, 4.52; N, 5,68.

EXAMPLE 2

2-[(Methylamino)sulfonyl]-benzo[b]thiophene-3-acetic acid

To a solution of N-3-dimethyl-benzo[b]thiophene-2-sulfonamide (1.0 g, 4.15 mmoles) in dry tetrahydrofuran (75 ml) was added a 2.0M solution of n-butyl-lithium in hexane (4.6 ml, 9.13 mmoles) at 0° C. The reaction mixture was stirred at 0° C. for 30 minutes, warmed to 15° C. for 10 minutes and then cooled to −20° C. Dry carbon dioxide gas was then bubbled in for 2 hours. The reaction mixture was poured into water, acidified, and then extracted with ethyl acetate. The organic extract was washed with water, dried (magnesium sulfate), and then concentrated in vacuo. The resulting solid was triturated using ether:hexane to give 633 mg (54%) of analytically pure title compound, mp 190°–192° C.; ms:m/e 285 (m+, 7), 241 (8), 176 (13), 162 (24), 146 (100); $^1$H-nmr (deuteriochloroform:dimethylsulfoxide-d$_6$): δ7.96 (m,2H), 7.56 (m,2H), 6.93 (m,1H), 433 (s,2H), 2.76 (d,3H); ir (potassium bromide): 3323, 2942, 1705, cm $^{-1}$.

Anal. Calcd. for $C_{11}H_{11}NO_4S_2$: C, 46.30; H, 3.89; N, 4.91. Found: C, 46.28; H, 3.90; N, 4,82.

EXAMPLE 3

2-Methyl-2H-[1]benzothieno[3,2-e]-1,2-thiazine-3-(4H)-one-1,1-dioxide

A solution of 2-[(Methylamino)sulfonyl]-benzo[b]thiophene-3-acetic acid (450 mg, 1.58 mmoles) and p-toluenesulfonic acid (45 mg) in xylenes (100 ml) was refluxed in a Dean-Stark trap for 6 hours. The solvent was evaporated and the resulting solid recrystallized from isopropanol to give the title compound (318 mg) in a yield of 765, mp 175°–178° C.; ms:m/e 267 (m+,25), 210(8), 160(5), 146(100); $^1$H-nmr(deuteriochloroform): δ7.96 (m,1H), 7,80 (m,1H), 7.58 (m,2H), 4.22 (s,2H), 3.38 (5,3H); ir (potassium bromide): 1700 cm$^{-1}$.

Anal. Calcd. for $C_{11}H_9NO_3S_2$: C, 49.42; H, 3.39; N, 5.24. Found: C, 49.71; H, 3.40; N, 5.20.

EXAMPLE 4

N-Aryl-3,4-dihydro-2-methyl-1,3-oxo-2H-[1]benzothieno[3,2-e]-1,2-thiazine-4-carboxamide-1,1-dioxides A. General Procedure To a solution of 2-methyl-2H-[1]benzothieno[3,2-e]-1,2-thiazine-3-(4H)-one-1,1-dioxide (500 mg, 1.87 mmoles) in dry dimethylformamide (20 ml) was added dry triethylamine (0.29 ml, 210 mg, 2.06 mmoles) at ambient temperature. The reaction mixture was stirred for 5 minutes and arylisocyanate (2.06 mmoles) was then added. The reaction mixture was then stirred for 5 hours, poured into ice water and acidified. The resulting precipitate was filtered, washed with water, and air dried. Recrystallization from an appropriate solvent, indicated below, gave an analytically pure compound.

B.

3,4-Dihydro-2-methyl-1,3-oxo-N-phenyl-2H-[1]benzothieno[3,2-e]-1,2-thiazine-4-carboxamide-1,1-dioxide Using phenyl isocyanate as the aryl isocyanate, the title compound was obtained in 66% yield as white needles (ethanol:methylene chloride) mp 233°–236°; ms:m/e 267(54), 162(10), 146(100) 119(86); $^1$H-nmr(dimethylsulfoxide-d$_6$):δ11.20(s,1H), 8.30–7.12 (m,9H), 5.74 (s,1H), 3.30 (s,3H); ir(potassium bromide):νNH 3294, νCO 1693, 1658 cm$^{-1}$.

Anal. Calcd. for $C_{18}H_{14}N_2O_4S_2$: C, 55.95; H, 3.65; N, 7.25. Found: C, 55.48; H, 3.55; N, 7.21.

C.

N-(4-Fluorophenyl)-3,4-dihydro-2-methyl-1,3-oxo-2H-[1]benzothieno[3,2-e]-1,2-thiazine-4-carboxamide-1,1-dioxide Using 4-fluorophenyl isocyanate as the aryl isocyanate, the title compound was obtained in 65% yield as white needles (isopropanol:methylene chloride) mp 250°–253°; ms:m/e 404 (m+,2), 267(100), 146(56), 137(38); $^1$H-nmr(dimethylsulfoxide-d$_6$):δ11.30 (s,1H), 8.34–7.22 (m,8H), 5.72 (s,1H), 3.32 (s,3H); ir(potassium bromide):νNH 3300, νCO 1696, 1657 cm⁻¹.

Anal. Calcd. for C₁₈H₁₃N₂O₄S₂F: C, 53.46; H, 3.24; N, 693. Found: C, 53.31; H, 3.30; N, 6.63.

D.
N-(4-Bromophenyl)-3,4-dihydro-2-methyl-1,3-oxo-2H-[1]benzothieno[3,2-e]-1,2-thiazine-4-carboxamide-1,1-dioxide Using 4-bromophenyl isocyanate as the aryl isocyanate, the title compound was obtained in 68% yield as white needles (isopropanol:methylene chloride) mp 245°–247°; ms:m/e 267(76), 197(40), 171(34) 162(22), 146(100); ¹H-nmr(dimethylsulfoxide-d₆):δ11.40 (s,1H), 8.34–7.64 (m,8H), 5.72 (s,1H), 3.32 (s,3H); ir (potassium bromide):νNH 3241, νCO 1697, 1652 cm⁻¹.

Anal. Calcd. for C₁₈H₁₃N₂O₄S₂Br: C, 46.46; H 2.82; N, 6.02. Found: C, 45.33; H, 2.81; N, 5.76.

E.
N-(4-trifluoromethylphenyl)-3,4-dihydro-2-methyl-1,3-oxo-2H-[1]benzothieno[3,2-e]-1,2-thiazine-4-carboxamide-1,1-dioxide Using 4-trifluoromethylphenyl isocyanate as the aryl isocyanate, the title compound was obtained in 65% yield as white needles (isopropanol:methylene chloride) mp 240°–243°; ms:m/e 267(21), 187(69), 168(18) 159(23), 146(100); ¹H-nmr(dimethylsulfoxide-d₆):δ11.62 (s,1H), 8.34–7.54 (m,8H), 5.76 (s,1H), 3.32 (s,3H); ir(potassium bromide):νNH 3257, νCO 1698, 1655 cm⁻¹.

Anal. Calcd. for C₁₉H₁₃N₂O₄S₂F₃: C, 50.72; H, 2,88; N, 6.16. Found: C, 49.87; H, 2.87; N, 6.35.

F.
N-(2-Methyl-4-nitrophenyl)-3,4-dihydro-2-methyl-1,3-oxo-2H-[1]benzothieno[3,2-e]-1,2-thiazine-4carboxamide-1,1-dioxide Using 2-methyl-4-nitrophenyl isocyanate as the aryl isocyanate, the title compound was obtained in 55% yield as white needles (isopropanol) mp 268°–270°; ms:m/e 267 (23), 178(61), 146(100); ¹H-nmr(dimethylsulfoxide-d₆):δ10.78 (s,1H), 8.32–7.72 (m,7H), 6.06 (s,1H), 3.02 (s,3H), 2.42 (s,3H); ir(potassium bromide):νNH 3377, νCO 1718, 1681 cm⁻¹.

Anal. Calcd. for C₁₉H₁₅N₃O₆S₂: C, 51.23; H, 3.39; N, 9.43. Found: C, 50.35; H, 3.30; N, 9.33.

G.
N-(2,4-Difluorophenyl)-3,4-dihydro-2-methyl-1,3-oxo-2H[1]benzothieno[3,2-e]-1,2-thiazine-4-carboxamide-1,1-dioxide Using 2,4-difluorophenyl isocyanate as the aryl isocyanate, the title compound was obtained in 66% yield as white needles (isopropanol:methylene chloride) mp 255°–258°; ms:m/e 267(61), 203(14), 174(14), 160(13), 155(69), 146(100); ¹H-nmr(dimethylsulfoxide-d₆):δ11.02 (s,1H), 8.32–7.08 (m,7H), 5.98 (s,1H), 3.32 (s,3H); ir(-potassium bromide):νNH 3365, νCO 1712, 1681 cm⁻¹.

Anal. Calcd. for C₁₈H₁₂N₂O₄S₂F₂: C, 51.18; H, 2,86; N, 6.63. Found: C, 51.42; H, 2.93; N, 6.89.

EXAMPLE 5

The title compounds of Examples 4B–4G were assayed according to the method of Jakschick et al. described above. The compounds were found to have inhibitory activity against cyclooxygenase or 5-lipoxygenase or both.

I claim:

1. A compound of the formula

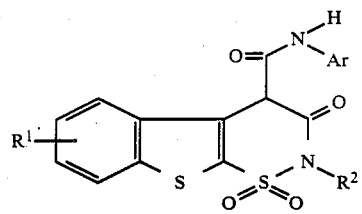

I or a pharmaceutically acceptable salt thereof wherein
R¹ is hydrogen, halogen or C₁ to C₄ alkyl;
r² is hydrogen or C₁ to C₄ alkyl; and
Ar is phenyl or phenyl substituted with one or more substituents selected from C₁ to C₄ alkyl, halo, trifluoromethyl, nitro, hydroxyl, halophenyl, or C₁ to C₄ alkoxy.

2. A compound of the formula I according to claim 1 wherein R¹ is hydrogen.

3. A compound of the formula I according to claim 1 wherein R² is methyl.

4. A compound of the formula I according to claim 1 wherein R¹ is hydrogen and R² is methyl.

5. A compound according to claim 1, said compound being selected from the group consisting of
3,4-Dihydro-2-methyl-1,3oxo-N-phenyl-2H-[1]benzothieno[3,2-e]-1,2-thiazine-4-carboxamide-1,1-dioxide;
N-(4-Fluorophenyl)-3,4-dihydro-2-methyl-1,3-oxo-2H-[1]benzothieno[3,2-e]-1,2-thiazine-4-carboxamide-1,1-dioxide;
N-(4-Bromophenyl)-3,4-dihydro-2-methyl-1,3-oxo2H-[1]benzothieno[3,2-e]-1,2-thiazine-4-carboxamide-1,1-dioxide;
N-(4-trifluoromethylphenyl)-3,4-dihydro-2-methyl-1,3-oxo-2H-[1]benzothieno[3,2-e]-1,2-thiazine-4-carboxamide-1,1-dioxide;
N-(2-Methyl-4-nitrophenyl)-3,4-dihydro-2-methyl--1,3-oxo-2H-[1]benzothieno[3,2-e]-1,2-thiazine-4-carboxamide-1,1-dioxide; and
N-(2,4-Difluorophenyl)-3,4-dihydro-2-methyl-1,3-oxo-2H[1]benzothieno[3,2-e]-1,2-thiazine-4-carboxamide-1,1-dioxide; and
pharmaceutically acceptable salts of the foregoing compounds.

6. A pharmaceutical composition for the treatment of inflammation, arthritis, allergy, psoriasis, asthma, bronchitis, pulmonary hypertension, pulmonary hypoxia, peptic ulcers, inflammatory bowel disease or cardiovascular spasm comprising an amount of a compound of claim 1 effective in treating one of the foregoing and a pharmaceutically acceptable carrier.

7. A composition according to claim 6, wherein R¹ is hydrogen.

8. A composition according to claim 6, wherein R² methyl.

9. A composition according to claim 6, wherein R¹ is hydrogen and R² is methyl.

10. A method of treating inflammation, arthritis, allergy, bronchitis, pulmonary hypertension, pulmonary hypoxia, peptic ulcers, inflammatory bowel disease, cardiovascular spasm, psoriasis or asthma comprising administering to a patent in need of such treatment an amount of a compound of claim 1 effective in treating one of the foregoing.

11. A method according to claim 10, wherein R¹ is hydrogen.
12. A method according to claim 10, wherein R² is methyl.
13. A method according to claim 10, wherein R¹ is hydrogen and R² is methyl.
14. A compound of the formula
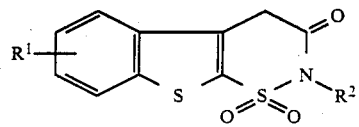
wherein
R¹ is hydrogen, halogen or $C_1$ to $C_4$ alkyl and
R² is hydrogen or $C_1$ to $C_4$ alkyl.
* * * * *